United States Patent
Lary

(10) Patent No.: US 6,951,566 B2
(45) Date of Patent: Oct. 4, 2005

(54) RECIPROCATING CUTTING AND DILATING BALLOON

(75) Inventor: Banning Gray Lary, Miami, FL (US)

(73) Assignee: SciMed Life Systems, Inc., Maple Grove, MN (US)

( * ) Notice: Subject to any disclaimer, the term of this patent is extended or adjusted under 35 U.S.C. 154(b) by 342 days.

(21) Appl. No.: 10/330,926

(22) Filed: Dec. 27, 2002

(65) Prior Publication Data

US 2003/0144677 A1 Jul. 31, 2003

Related U.S. Application Data

(60) Provisional application No. 60/368,009, filed on Mar. 27, 2002, provisional application No. 60/356,273, filed on Feb. 12, 2002, and provisional application No. 60/351,893, filed on Jan. 25, 2002.

(51) Int. Cl.[7] .............................................. A61B 17/22
(52) U.S. Cl. .................................................. 606/159
(58) Field of Search ............................... 606/159, 170, 606/194, 167; 604/103.07, 103.08, 96.01

(56) References Cited

U.S. PATENT DOCUMENTS

| | | |
|---|---|---|
| 4,273,128 A | 6/1981 | Lary |
| 4,787,388 A | 11/1988 | Hofmann |
| 5,176,693 A | 1/1993 | Pannek, Jr. |
| 5,192,291 A | 3/1993 | Pannek, Jr. |
| 5,196,024 A | 3/1993 | Barath |
| 5,224,945 A | 7/1993 | Pannek, Jr. |
| 5,372,601 A | 12/1994 | Lary |
| 5,556,405 A | 9/1996 | Lary |
| 5,697,944 A | 12/1997 | Lary |
| 5,792,158 A | 8/1998 | Lary |
| 6,258,108 B1 | 7/2001 | Lary |
| 6,632,231 B2 * | 10/2003 | Radisch, Jr. ................. 606/159 |
| 6,746,463 B1 * | 6/2004 | Schwartz ..................... 606/159 |

* cited by examiner

*Primary Examiner*—(Jackie) Tan-Uyen T. Ho
(74) *Attorney, Agent, or Firm*—Nydegger & Associates

(57) ABSTRACT

An apparatus for incising a stenosis within a vascular conduit of a patient includes an inflatable balloon attached to an elongated catheter that defines a longitudinal axis. The distal end of the balloon includes a tapered section and at least one incising blade is attached to the tapered section. Each incising blade is oriented on the tapered section with the proximal end of the blade radially distanced from the longitudinal axis at a distance $r_1$ and the distal end of the incising blade radially distanced from the longitudinal axis at a distance $r_2$. After the balloon has been inflated, each incising blade is oriented with $r_1 > r_2$ to position the incising blades at an angle relative to the axis. This cooperation of structure allows the incising blades to cut an incision into a stenosis during axial advancement of the inflated balloon.

17 Claims, 4 Drawing Sheets

RECIPROCATING CUTTING AND DILATING BALLOON

This application claims the benefit of U.S. Provisional Application No. 60/351,893 filed Jan. 25, 2002, U.S. Provisional Application No. 60/356,273 filed Feb. 12, 2002 and U.S. Provisional Application No. 60/368,009 filed Mar. 27, 2002.

FIELD OF THE INVENTION

The present invention relates generally to surgical instruments. More particularly, the present invention pertains to surgical instruments for removing an obstruction in, or for enlarging the orifice of a vascular conduit or connective duct. The present invention is particularly, though not exclusively, useful for incising a stenosis within a vascular conduit and subsequently dilating the incised stenosis to increase bloodflow through the conduit.

BACKGROUND OF THE INVENTION

Coronary artery stenosis is primarily due to deposits of cholesterol, calcium and fibrotic tissue. The fibrotic tissue is usually the dominate of the three components and is a tightly composed matrix that, when incised, maintains its integrity on each side of the incision. Dilation of stenoses using standard angioplasty balloons has enjoyed widespread acceptance in the treatment of stenoses, however, this treatment protocol suffers from a high rate of restenosis. Recent studies, however, indicate that restenosis can be prevented by first incising the material that is creating the stenosis followed by dilation of the incised stenosis. After incision, a stenosis is more easily flattened, and the likelihood of damaging the artery during dilation is reduced. In most applications, incision lengths of up to approximately fifteen millimeters (15 mm) are required, followed by dilation of the incised stenosis.

Heretofore, developments have been made to equip angioplasty balloons with cutting edges, or atherotomes, which are intended to incise a stenosis subsequent to a dilation procedure. For example, U.S. Pat. No. 5,196,024 to Barath entitled "BALLOON CATHETER WITH CUTTING EDGE," which is assigned to the assignee of the present invention, discloses an inflatable angioplasty balloon having a number of atherotomes mounted longitudinally on the surface of the balloon. During inflation of the Barath balloon, the atherotomes move radially to induce a series of longitudinal cuts into the surface of the stenotic material. However, when incisions of up to fifteen millimeters (15 mm) are prescribed, the Barath design requires long atherotomes due to the fact that the Barath blades only cut during radial blade movements. Unfortunately, these long, rigid blades (i.e. 10–15 mm) reduce the flexibility of the apparatus making it more difficult to guide the dilation balloon and blades through the vascular conduits to the site of the stenosis. In general, blades longer than about 4 mm have a tendency to reduce the flexibility of an apparatus such that a considerable number of operations fail due to the inability of the surgeon to navigate the tortuous vascular conduits and position the blades and balloon at the site of the stenosis.

In light of the above, it is an object of the present invention to provide an apparatus for incising a stenosis in a vascular conduit of a patient. It is a further object of the present invention to provide an apparatus for incising a stenosis having relatively short incising blades that, due to their small size can be easily guided through tortuous vascular conduits to the site of the stenosis. It is still another object of the present invention to provide an apparatus for incising a stenosis that can be adjusted, in situ to vary the incision depth. It is yet another object of the present invention to provide an apparatus for incising a stenosis that car also dilate the incised stenosis. It is another object of the present invention to provide an apparatus for incising a stenosis which is relatively simple to manufacture, is easy to use, and is comparatively cost effective.

SUMMARY OF THE PREFERRED EMBODIMENTS

The present invention is directed to an apparatus for incising and dilating a stenosis within a vascular conduit of a patient. More specifically, the present invention is directed to an apparatus for incising a stenosis with relatively short incising blades that, due to their small size, can be easily guided through the bends and curves of the narrow vascular conduits to the site of the stenosis. For the present invention, the apparatus includes an inflatable balloon that is attached to the distal end of a catheter. The catheter is elongated and defines a longitudinal axis in the direction of elongation. At the distal end of the catheter, the balloon extends axially from a distal end to a proximal end and is formed with an external surface. Also for the present invention, the balloon includes a tapered section that can extend to the distal end of the balloon. More specifically, due to the tapered section, the balloon narrows in the distal direction toward the distal end of the balloon. Consequently, within the tapered section, the external surface of the balloon includes a first point radially distanced from the longitudinal axis at a relatively large distance $d_1$ and a second point, distal to the first point, that is radially distanced from the longitudinal axis at a relatively small distance $d_2$ ($d_1 > d_2$), when the balloon is inflated.

In accordance with the present invention, the apparatus further includes one or more incising blades, with each incising blade having a proximal end and a distal end. Each blade is attached to the external surface of the balloon, extending outwardly from the external surface and terminating in a cutting edge. More specifically, each incising blade is attached to the tapered section of the balloon. For the present invention, each incising blade is oriented with the proximal end of the blade radially distanced from the longitudinal axis at a distance $r_1$ and the distal end of the incising blade radially distanced from the longitudinal axis at a distance $r_2$, with $r_1 > r_2$. As a consequence, the balloon can be inflated to deploy each incising blade into a position where the blade is at an angle relative to the longitudinal axis of the catheter. This cooperation of structure allows the incising blades to cut an incision into a stenosis during axial advancement of the inflated balloon.

In one embodiment of the present invention, the balloon, when inflated, includes a tapered section that is conically shaped. In this embodiment, incising blades formed with substantially straight cutting edges are used. However, for this embodiment, each incising blade is formed with a curved advancing edge at the distal end of the incising blade to allow the incising blade to contact and cut a stenosis over the entire range of balloon inflation pressures. In another embodiment of the present invention, a balloon having a non-conical tapered section is used. Specifically, the external surface of the tapered section in this embodiment is shaped as a surface of revolution defined by the rotation of a curve about the longitudinal axis. For this embodiment, incising blades having cutting edges that are continuously curved from the distal end of the blade to the proximal end of the blade can be used.

In both the straight blade and curved blade embodiments, the balloon can be shaped wherein a portion of the balloon extends to a greater radial distance than the blades, after the balloon has been inflated. More specifically, the tapered section can extend proximally from the proximal end of each blade. With this cooperation of structure, there will be at least one point on the balloon that is distanced from the longitudinal axis at a distance d with $d>r_1$ after the balloon has been inflated. This cooperation of structure prevents the blades from cutting into or through the wall of the vascular conduit, while allowing the blades to incise a stenosis that protrudes from the wall of the vascular conduit and into the lumen of the vascular conduit.

To further allow the apparatus to be easily navigated through the vascular conduits of a patient, the catheter can include a flexible coil. In a particular embodiment of the present invention, the flexible coil is positioned proximal to the balloon. In another embodiment of the present invention, the balloon is formed with a cylindrical section that is positioned proximal to the tapered section with at least a portion of the flexible coil positioned inside the balloon. The flexible coil provides lateral flexibility to the apparatus, allowing the blades and at least a portion of the balloon to deflect from the proximal portion of the apparatus during advancement and withdrawal of the apparatus through the vascular conduits. On the other hand, the flexible coil provides good axial stiffness allowing the catheter to be pushed through the vascular conduits. Additionally, the coil is capable of transmitting the axial force required to push the incising blades through a stenosis during an incision.

In operation, the balloon is first deflated, allowing each blade to assume a position adjacent and parallel to the longitudinal axis. In a particular implementation, each blade is further positioned between adjacent balloon folds to prevent exposure of the cutting edges to the walls of the vascular conduits while the apparatus is navigated through the vascular conduits of the patient. With the balloon deflated, the distal end of the apparatus is inserted into a vascular conduit such as a peripheral artery and advanced through the vasculature until the blades and balloon are positioned in front of a stenosis. For this purpose, a guidewire can be used to establish a mechanical pathway to assist the distal end of the apparatus to the site of the stenosis. Next, the balloon is at least partially inflated causing the balloon and incising blades to move outwardly together in a radial direction from the longitudinal axis. In greater detail, the proximal end of each blade moves a greater radial distance than the distal end of the blade during inflation, positioning the proximal end of each blade at a greater radial distance from the longitudinal axis than the distal end of each incision blade. It is to be appreciated that the proximal end of each blade can be moved to a selected radial distance by controlling the inflation pressure within the balloon.

With the blades deployed in this manner, the apparatus can then be axially advanced to push one or more of the incising blades through the stenosis. Next, if required, the apparatus can be axially withdrawn until the blades are once again positioned in front of the stenosis. At this point, the inflation pressure can be adjusted to increase/decrease the radial distance between the longitudinal axis than the proximal end of each incision blade, and thus modify the incision depth. With the blades adjusted for the proper incision depth, the apparatus can once again be axially advanced to push the incising blades through the stenosis. This process can then be repeated as many times as desired.

Once the stenosis has been satisfactorily incised, the apparatus can be used to dilate the incised stenosis. Specifically, the apparatus can be axially advanced/withdrawn until a selected portion of the balloon, such as a portion of the balloon proximal to the tapered section, is positioned adjacent to the stenosis. In some cases, the balloon may need to be at least partially deflated (relative to the inflation pressure used for incising) to position the balloon for dilation. With the proximal portion of the balloon positioned adjacent the stenosis, the balloon can be expanded to dilate the incised stenosis. After the stenosis has been incised and dilated, the balloon can be deflated to thereby allow the apparatus to be moved for treatment of another stenosis or withdrawn from the patient's body.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
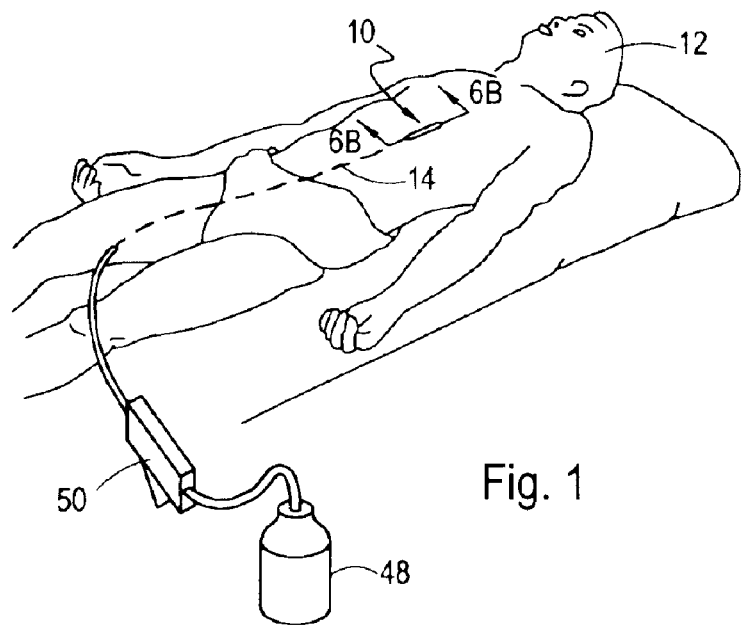
FIG. 1 is a simplified, schematic view showing an apparatus in accordance with the present invention operationally positioned in a patient to incise and dilate a stenosis in an upper body artery.

Referring initially to FIG. 1, an apparatus for incising and dilating a stenosis within a vascular conduit is shown and generally designated 10. More specifically, the apparatus 10 is shown positioned for treatment of an upper body artery in a patient 12. Although the apparatus 10 is capable of treating a stenosis in an upper body artery such as a coronary artery, those skilled in the pertinent art will recognize that the use of the apparatus 10 is not limited to upper body arteries, but, instead can be used in vascular conduits and other ductal systems throughout the human body, and is also suitable for use in plants and animals.

Figure 2:
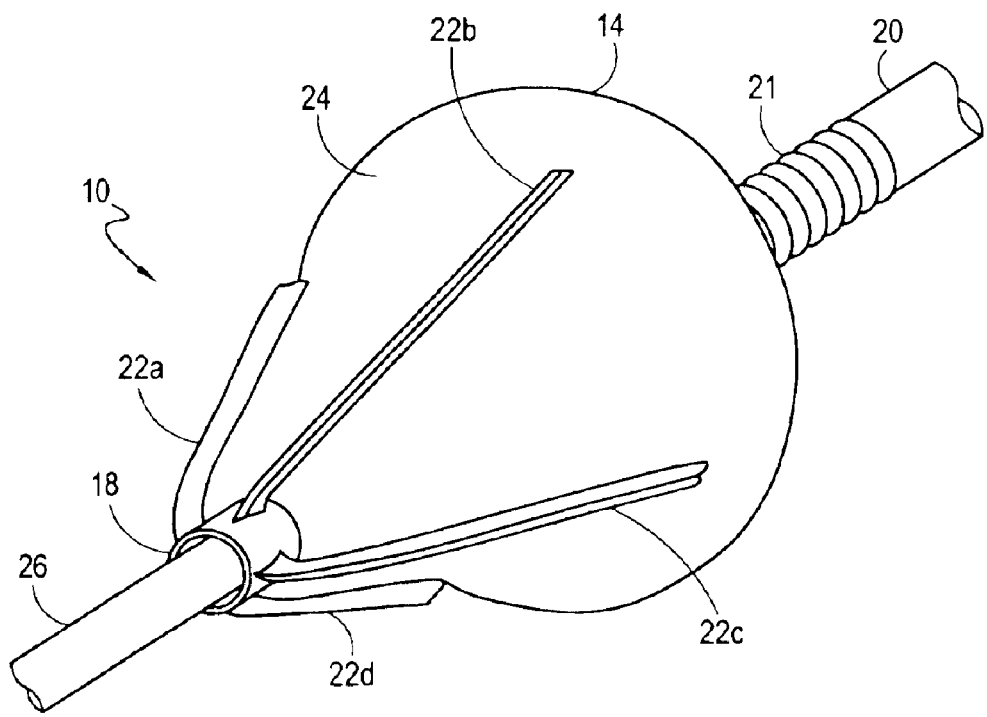
FIG. 2 is an enlarged perspective view of the distal portion of an apparatus in accordance with the present invention, shown after balloon inflation.

Referring now to FIG. 2, the distal end of the apparatus 10 is shown to include an inflatable balloon 14 that is attached to the distal end 18 of an elongated tubular catheter 20. As shown, the catheter 20 can include a flexible, helical coil 21 positioned proximal to the balloon 14. As further shown in FIG. 2, the apparatus 10 includes incising blades 22a–d that are attached to the external surface 24 of the balloon 14 and circumferentially distributed around the balloon 14. As further shown, the balloon 14 and catheter 20 (including the coil 21) are formed with a contiguous lumen to allow the balloon 14 and catheter 20 (including the coil 21) to travel over a guidewire 26.

Figure 3:
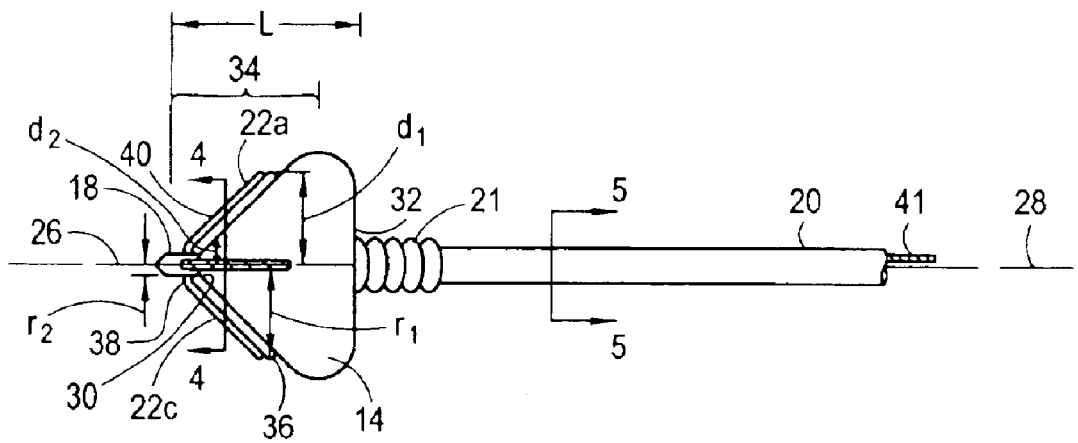
FIG. 3 is an enlarged elevation view of the distal portion of an apparatus in accordance with the present invention, shown after balloon inflation.

Referring now to FIG. 3, it can be seen that the elongated catheter 20 defines a longitudinal axis 28 in the direction of elongation. As further shown, the balloon 14 extends axially from a distal end 30 to a proximal end 32, defining a length L that is typically in the range of approximately five to six millimeters (5–6 mm). Also shown, the balloon 14 includes a tapered section 34 that extends to the distal end 30 of the balloon 14. More specifically, within the tapered section 34, the balloon 14 is conically shaped and narrows in the distal direction toward the distal end 30 of the balloon 14. Consequently, the inflated balloon 14 includes a first point radially distanced from the longitudinal axis 28 at a relatively large distance $d_1$ and a second point, distal to the first point, that is radially distanced from the longitudinal axis 28 at a relatively small distance $d_2$ ($d_1 > d_2$), as shown.

Figure 4:
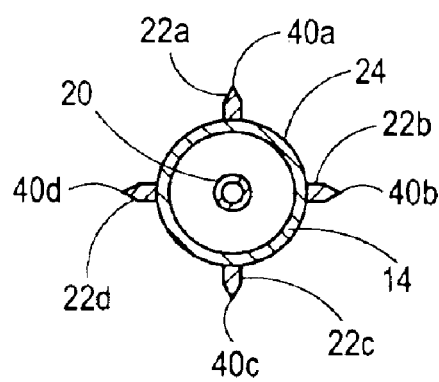
FIG. 4 is a cross-sectional view of the balloon and incising blades as seen along line 4—4 in FIG. 3.

With continued reference to FIG. 3, it can be seen that each incising blade 22 extends from a proximal end 36 to a distal end 38 defining a length therebetween that is typically in the range of approximately two to four millimeters (2–4 mm). As shown, each incising blade 22 is positioned on the tapered section 34 of the balloon 14. As best seen in FIG. 4, each blade 22a–d is attached to the external surface 24 of the balloon 14 and extends outwardly from the external surface 24 to respective cutting edge 40a–d. Referring back to FIG. 3, it can be seen that each incising blade 22 is formed with a substantially straight cutting edge 40 having a curved advancing edge at the distal end 30 to allow the incising blade 22 to contact and cut a stenosis over the entire range of balloon 14 inflation pressures. It can be further seen that after the balloon 14 has been inflated, each incising blade 22 is oriented with the proximal end 36 of the blade 22 radially distanced from the longitudinal axis 28 at a distance $r_1$ and the distal end 38 of the incising blade 22 radially distanced from the longitudinal axis 28 at a distance $r_2$, with $r_1 > r_2$. As a consequence of this orientation, the balloon 14 can be inflated to deploy each incising blade 22 into a position where the blade 22 is at an angle relative to the longitudinal axis 28. This cooperation of structure allows the incising blades 22 to cut an incision into a stenosis during axial advancement of the inflated balloon 14.

Figure 5:
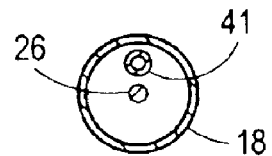
FIG. 5 is a cross-sectional view of the catheter showing the inflation/deflation tube as seen along line 5—5 in FIG. 3.

Continuing with reference to FIG. 3, it can be seen that the inflated balloon 14 is shaped wherein a portion of the balloon 14 extends to a greater radial distance from the longitudinal axis 28 than the proximal end 36 of each blade 22. In greater detail, FIG. 3 shows that the tapered section 34 can extend proximally from the proximal end 36 of each blade 22. With this cooperation of structure, there will be at least one point on the inflated balloon 14 that is distanced from the longitudinal axis 28 at a distance greater than $r_1$. This cooperation of structure prevents the blades 22 from cutting into or through the wall of the vascular conduit, while allowing the blades 22 to incise a stenosis that protrudes from the wall of the vascular conduit and into the lumen of the vascular conduit. With cross reference to FIGS. 3 and 5, it can be seen that an inflation tube 41 extends through the catheter 20 to allow for inflation/deflation of the balloon 14 from an extracorporeal location.

Figure 6A:
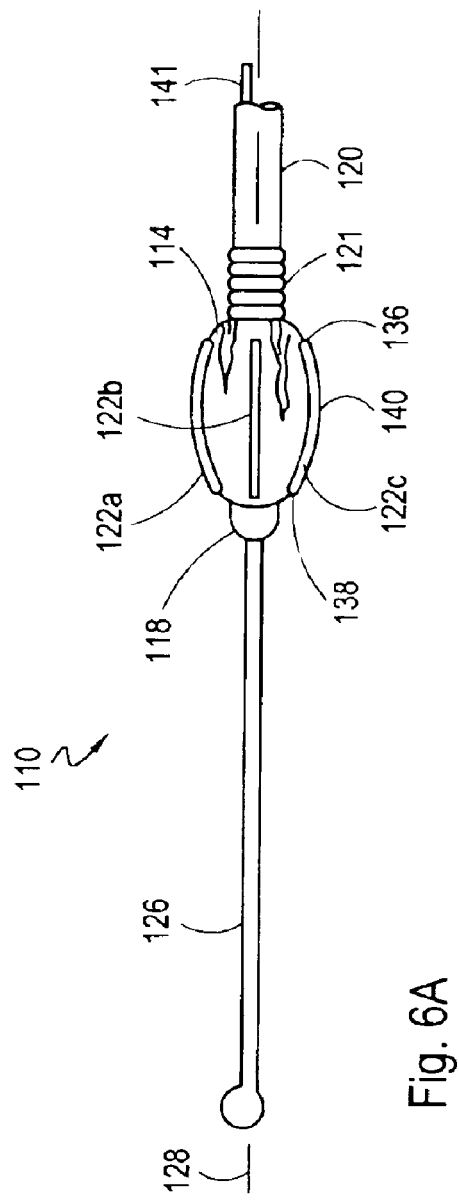
FIG. 6A is an enlarged elevation view of the distal portion of another embodiment in accordance with the present invention having blades with curved cutting edges, shown with the balloon in the deflated configuration.
Figure 6B:
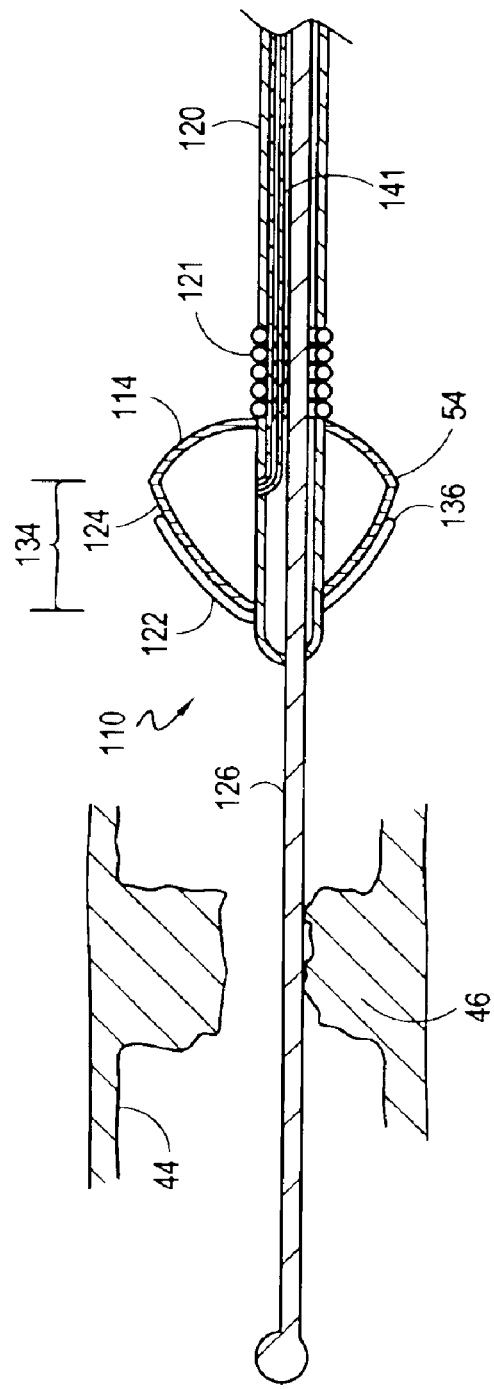
FIG. 6B is a cross-sectional view along line 6B—6B in FIG. 1 of the distal portion of the apparatus shown in FIG. 6A, shown after balloon inflation.

Referring now to FIGS. 6A and 6B, another embodiment of the apparatus (labeled 110) is shown. As further shown, the apparatus 110 includes a balloon 114 having a non-conical tapered section 134 attached to the distal end 118 of a catheter 120 that includes a flexible, helical coil 121 positioned proximal to the balloon 114. It is to be appreciated from FIG. 6B, the external surface 124 of the tapered section 134 is shaped as a surface of revolution defined by the rotation of a curve about the longitudinal axis 128. For this embodiment, incising blades 122a–c have cutting edges 140 that are continuously curved from the distal end 138 to the proximal end 136 are used.

Figure 7:
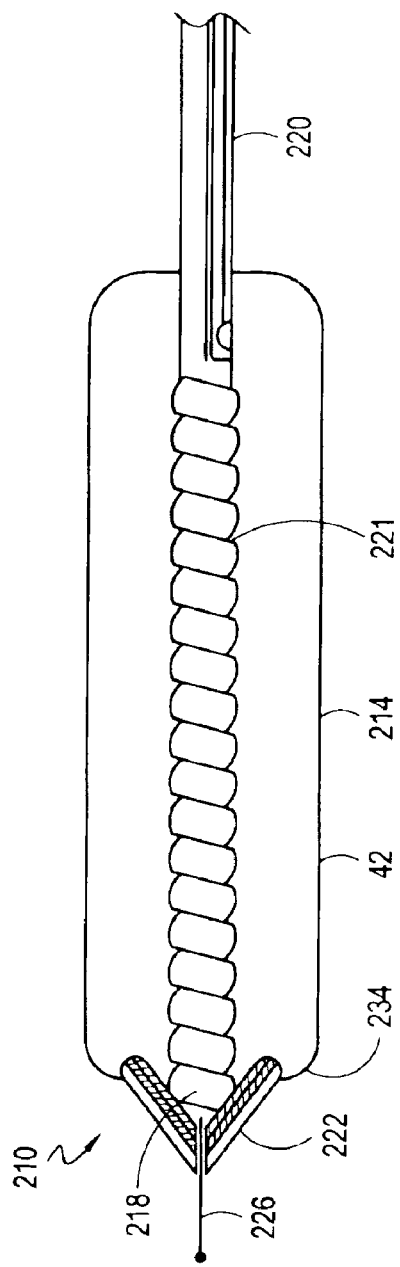
FIG. 7 is schematic view of the distal portion of still another embodiment in accordance with the present invention having a balloon with a tapered section for deploying the incising blades and a cylindrical section for dilation.

Referring now to FIG. 7, another embodiment of the apparatus (labeled 210) is shown. As further shown, the apparatus 210 includes a balloon 214 having tapered section 234 and a cylindrical dilation section 42 positioned proximal to the tapered section 234. It can be further seen that the balloon 214 is attached to the distal end 218 of a catheter 220 that includes a flexible, helical coil 221. In this embodiment, as shown, the coil 221 is positioned inside the balloon 214. Incising blades 222 are mounted on the tapered section 234 of the balloon 214. It is to be appreciated that the catheter 220, including the helical coil 221, establish a lumen to allow the catheter 220, balloon 214 and blades 222 to travel over guidewire 226.

OPERATION

To use the apparatus 10, 110, 210 of the present invention, access to the vasculature is obtained by piercing an opening in a peripheral artery, such as the femoral artery (see FIG. 1) and positioning a sheath (not shown) within the artery. Next, a guidewire, such as guidewire 126 shown in FIGS. 6A and 6B, is inserted into the opening and advanced through the patient's vasculature. The guidewire 126 is advanced and steered into the vascular conduit 44 of interest and then advanced past the stenosis 46 requiring treatment. With the guidewire 126 in place, the balloon 114 is first collapsed into the deflated configuration as shown in FIG. 6A. As shown in FIG. 6A, in the deflated configuration, each blade 122a–c is positioned adjacent and substantially parallel to the longitudinal axis 128, allowing the apparatus 110 to fit into a small access opening and to more easily transit through the vasculature.

Figure 8:
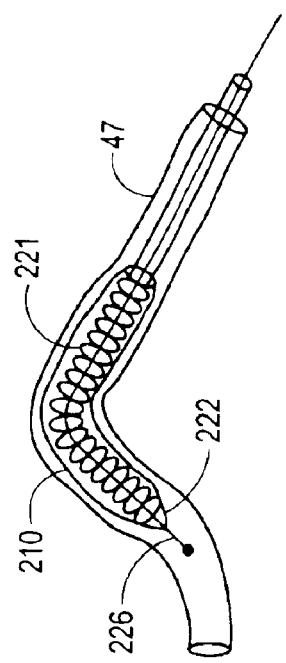
FIG. 8 is a schematic view of the apparatus shown in FIG. 8, shown positioned in a curved vascular conduit.

Next, the apparatus 110 is threaded onto the guidewire 126 at an extracorporeal location, inserted into the access opening and advanced over the guidewire 126 until the balloon 114 is positioned in the vascular conduit 44 of interest and in front of the stenosis 46 requiring treatment. During advancement of the apparatus (such as apparatus 210 shown in FIG. 8) through the vasculature, the flexible coil 221 provides lateral flexibility to the apparatus 210, allowing the blades 222 to deflect from the proximal portion of the apparatus 210. This deflection allows the apparatus 210 to navigate through acute angles in a vascular conduit 47, as shown in FIG. 8.

Continuing now with cross reference to FIGS. 1 and 6A, once the balloon 114 is positioned in front of the stenosis 46, the balloon 114 is inflated to deploy the incising blades 122. In greater detail, inflation fluid from fluid source 48 can be passed under control of controller 50 through inflation tube 141 and into the balloon 114. It is to be appreciated that the proximal end 136 of each blade 122 can be moved to a selected radial distance by controlling the inflation pressure within the balloon 114.

With the blades 122 deployed in this manner, the apparatus 110 can then be axially advanced to push one or more of the incising blades 122 through the stenosis 46. If required, a reciprocating force can be applied to the apparatus 110 from the periphery to pass the blades 122 through the stenosis 46. During advancement of the blades 122 through the stenosis 46, the flexible coil 121 provides good axial stiffness, and thus effectively transmits the axial force necessary to incise the stenosis 46. After initial incision, if desired, the apparatus 110 can be axially withdrawn until the blades 122 are once again positioned in front of the stenosis 46. At this point, the inflation pressure can be adjusted to modify the incision depth. With the blades 122 adjusted for the proper incision depth, the apparatus 110 can once again be axially advanced to push the incising blades 122 through the stenosis 46. This process can then be repeated as many times as desired.

Once the stenosis 46 has been satisfactorily incised, the apparatus 110 can be used to dilate the incised stenosis 46. Specifically, the apparatus 110 can be axially advanced until the largest diameter portion of the balloon (i.e. point 54 on balloon 114) passes through and dilates the stenosis 46. Alternatively, with the balloon 114 partially inflated, the balloon 114 can be positioned with the largest diameter portion of the balloon (i.e. point 54 on balloon 114) within the stenosis 46. Once positioned, the balloon 114 can be further distended to dilate the stenosis 46. When the embodiment shown in FIGS. 7 and 8 is used, the cylindrical dilation section of the balloon 214 can be used to dilate a relatively long stenosis. After the stenosis 46 (see FIG. 6B) has been incised and dilated, the balloon 114 can be deflated to thereby allow the apparatus 110 to be moved for treatment of another stenosis or withdrawn from the patient's body.

While the particular apparatus and methods as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. An apparatus for incising a stenosis in a vascular conduit of a patient, said apparatus comprising:
   a catheter having a distal end and defining a longitudinal axis;
   an inflatable balloon mounted on said catheter proximate said distal end, said balloon formed with an external surface and being insertable into the vasculature of a patient for movement therein between a deflated configuration and an inflated configuration, said external surface having at least one section including a first point radially distanced from said longitudinal axis at a distance $d_1$ and a second point radially distanced from said longitudinal axis at a distance $d_2$ with $d_1 > d_2$ when said balloon is in said inflated configuration; and
   at least one incising blade having a proximal end and a distal end, said blade being attached to said external surface of said balloon and oriented with said proximal end of said incising blade at said first point and said distal end of said incising blade at said second point and wherein said incising blade is formed with the cutting edge and said cutting edge is substantially straight.

2. An apparatus as recited in claim 1 wherein said catheter comprises a flexible coil positioned proximal to said balloon to allow said apparatus to be navigated through the vasculature.

3. An apparatus as recited in claim 1 wherein said catheter comprises a flexible coil and at least a portion of said flexible coil is positioned within said balloon to allow said apparatus to be navigated through the vasculature.

4. An apparatus as recited in claim 1 wherein said first point is distanced further from said longitudinal axis than said proximal end of said incising blade ($d_1 > r_1$) when said balloon is in said inflated configuration.

5. An apparatus as recited in claim 1 wherein said incising blade is formed with the cutting edge and said cutting edge is curved.

6. An apparatus as recited in claim 1 wherein said incising blade defines a length between said proximal end and said distal end and said length is between approximately two millimeters (2 mm) and approximately four millimeters (4 mm).

7. An apparatus as recited in claim 1 wherein at least one incising blade is four incising blades.

8. An apparatus as recited in claim 1 wherein said catheter is formed with an inflation lumen to deliver an inflation fluid to said balloon.

9. An apparatus for incising a stenosis within a patient, said apparatus comprising:
   a catheter having a distal end and defining a longitudinal axis;
   an inflatable balloon formed with a tapered section and mounted on said catheter proximate said distal end, said balloon reconfigurable between a deflated configuration and an inflated configuration; and
   at least one incising blade having a proximal end and a distal end, said blade being attached to said tapered section of said balloon and oriented axially along a line with said proximal end of said incising blade being distanced from said longitudinal axis at a distance $r_1$ and said distal end of said incising blade being distanced from said longitudinal axis at a distance $r_2$ with $r_1 > r_2$ when said balloon is in said inflated configuration, and wherein said line includes a first point radially distanced from said longitudinal axis at a distance $d_1$ and a second point radially distanced from said longitudinal axis at a distance $d_2$ with $d_1 > d_2$ when said balloon is in said inflated configuration, and with $d_1 > r_1$ when said balloon is in said inflated configuration.

10. An apparatus as recited in claim 9 wherein said tapered section is conically shaped.

11. An apparatus as recited in claim 9 wherein said tapered section is shaped as a surface of revolution defined by the rotation of a curve about said longitudinal axis.

12. An apparatus as recited in claim 9 wherein said catheter comprises a flexible coil to allow said apparatus to be navigated through the vasculature.

13. An apparatus as recited in claim 9 wherein said incising blade defines a blade length between said proximal end and said distal end and said blade length is between approximately two millimeters (2 mm) and approximately four millimeters (4 mm) and wherein said balloon extends from a distal end to a proximal end and defines a balloon length between said proximal end and said distal end and said balloon length is between approximately five millimeters (5 mm) and approximately six millimeters (6 mm).

14. A method for incising a stenosis in the vasculature of a patient, said method comprising the steps of:
   providing an inflatable balloon defining an axis;
   mounting at least one incising blade having a proximal end and a distal end onto said balloon, with said incising blade being axially oriented along a line thereon;
   positioning said balloon adjacent said stenosis;

inflating said balloon to orient said incising blade wherein said proximal end of said incising blade is distanced from said longitudinal axis at a distance $r_1$ and said distal end of said incising blade is distanced from said longitudinal axis at a distance $r_2$, with $r_1 > r_2$, and wherein said line includes a first point radially distanced from said longitudinal axis at a distance $d_1$ and a second point radially distanced from said longitudinal axis at a distance $d_2$ with $d_1$ when said balloon is in said inflated configuration, and with $d_1 > r_1$ when said balloon is in said inflated configuration; and thereafter axially advancing said balloon in said vasculature to incise the stenosis with said incising blade.

15. A method as recited in claim 14 further comprising the steps of:

axially withdrawing said balloon; and re-advancing said balloon axially to further incise the stenosis.

16. A method as recited in claim 14 wherein said inflating step inflates said balloon to a first pressure and wherein said method further comprises the steps of inflating said balloon to a second pressure subsequent to said advancing step to dilate the incised stenosis.

17. A method as recited in claim 14 further comprising the steps of;

deflating said balloon; and axially withdrawing said balloon and incising blade to remove said balloon and incising blade from the patient.

* * * * *

UNITED STATES PATENT AND TRADEMARK OFFICE
CERTIFICATE OF CORRECTION

PATENT NO.    : 6,951,566 B2  
DATED         : October 4, 2005  
INVENTOR(S)   : Banning Gray Lary It is certified that error appears in the above-identified patent and that said Letters Patent is hereby corrected as shown below:

Column 2,
Line 4, delete "car" insert -- can --.

Column 9,
Line 9, delete "$d_1$" insert -- $d_1 > d_2$ --.

Signed and Sealed this

Sixth Day of December, 2005

JON W. DUDAS
*Director of the United States Patent and Trademark Office*